United States Patent
Bernard

(10) Patent No.: US 7,163,995 B2
(45) Date of Patent: Jan. 16, 2007

(54) LOW-VISCOSITY POLYISOCYANTE COMPOSITION HAVING HIGH FUNCTIONALITY AND METHOD FOR PREPARING SAME

(75) Inventor: Jean-Marie Bernard, Mornant (FR)

(73) Assignee: Rhodia Chimie, Boulogne-Billancourt (FR)

(*) Notice: Subject to any disclaimer, the term of this patent is extended or adjusted under 35 U.S.C. 154(b) by 34 days.

(21) Appl. No.: 10/508,940

(22) PCT Filed: Mar. 27, 2003

(86) PCT No.: PCT/FR03/00976

§ 371 (c)(1),
(2), (4) Date: Sep. 27, 2004

(87) PCT Pub. No.: WO03/080697

PCT Pub. Date: Oct. 2, 2003

(65) Prior Publication Data

US 2005/0154171 A1 Jul. 14, 2005

(30) Foreign Application Priority Data

Mar. 27, 2002 (FR) .................................. 02 03877

(51) Int. Cl.
*C08G 18/74* (2006.01)
(52) U.S. Cl. ............................ 528/73; 528/45; 528/67; 252/182.21; 544/222
(58) Field of Classification Search ................ 528/45, 528/67, 73; 252/182.21; 544/222
See application file for complete search history.

(56) References Cited

U.S. PATENT DOCUMENTS

| 4,324,879 A | 4/1982 | Bock et al. |
| 4,412,073 A | 10/1983 | Robin |
| 4,801,663 A | 1/1989 | Ueyanagi et al. |
| 4,810,820 A | 3/1989 | Slack et al. |
| 5,143,994 A | 9/1992 | Laas et al. |
| 5,750,629 A | 5/1998 | Laas et al. |
| 2004/0106762 A1 | 6/2004 | Charriere et al. |

FOREIGN PATENT DOCUMENTS

| DE | 19603245 A1 | 7/1997 |
| EP | 0478990 A1 | 4/1992 |
| EP | 0645411 A1 | 3/1995 |
| WO | 99/07765 A1 | 2/1999 |

OTHER PUBLICATIONS

Saunders et al.; Polyurethanes; Part I; 1962; p. 120.*

* cited by examiner

*Primary Examiner*—Rachel Gorr
(74) *Attorney, Agent, or Firm*—Buchanan Ingersoll & Rooney PC

(57) ABSTRACT

The invention concerns a polyisocyanate composition having high functionality, obtained by polycondensation of diisocyanate or triisocyanate monomers, comprising: (a) 0.5 to 30 wt % of compounds bearing a single uretidinedione function; (b) 0.5 to 45 wt. % of compounds bearing a single isocyanurate function; (c) at least 40 wt. % of a mixture of polyisocyanate compounds having a molecular weight not less than three times the average molecular weight of the isocyanate monomers having the smallest molecular weight and bearing at least two isocyanate functions, said mixture having a ratio of carbonyl functions belonging to a uretidinedione cycle/carbonyl functions belonging to an isocyanate cycle+carbonyl functions belonging to a uretidinedione cycle not less than 4%; (d) 0 to 25 wt. % of compounds bearing at least an isocyanate function other than (a), (b) and (c); and (e) 0 to 10% of impurities.

44 Claims, No Drawings

LOW-VISCOSITY POLYISOCYANTE COMPOSITION HAVING HIGH FUNCTIONALITY AND METHOD FOR PREPARING SAME

The invention relates to an optionally masked polyisocyanate composition of relatively low viscosity with a high mean functionality of at least 3 or more. The invention also relates to a process for preparing a low-viscosity polyisocyanate composition with a high mean functionality of isocyanate groups.

Masked or nonmasked polyisocyanate compositions with a mean functionality of greater than 2 are generally obtained by catalytic cyclotrimerization of diisocyanates and comprise compounds comprising isocyanurate groups.

Such compositions and processes for preparing them are disclosed in, for example, U.S. Pat. No. 4,324,879 and U.S. Pat. No. 4,412,073. Although these compositions have noteworthy properties, they have, however, a high viscosity which requires them to be diluted with organic solvents.

One of the solutions recommended for this purpose is to halt the cyclotrimerization reaction at a very low degree of trimerization in order to increase the amount of monoisocyanurate polyisocyanates and to reduce the amount of isocyanurate polyisocyanates containing more than one isocyanurate ring. Thus, patent U.S. Pat. No. 4,801,663 discloses a process for the cyclotrimerization of 1,6-hexamethylene diisocyanate (HDI) in which the trimerization is halted at a low degree of conversion.

The drawback of such a process is, however, a significant decrease in the overall yield of the reaction, which requires the removal from the final reaction product of a significant amount of unreacted monomers, the effect of which is to greatly increase the cost of the process.

Another solution provided (cf. U.S. Pat. No. 5,750,629) consists in subjecting the isocyanate monomers to a cyclodimerization reaction before, after or during the cyclotrimerization step, in order to produce a polyisocyanate composition having isocyanate compounds comprising isocyanurate groups and isocyanate compounds comprising uretidinedione (1,3-diazetidine-2,4-dione) groups, in particular monouretidinedione compounds.

The drawback of this process is, however, a reduction in the mean functionality with regard to NCO groups of the reaction product, due to a greater or lesser proportion of uretidinedione compounds.

Another solution recommended in U.S. Pat. No. 4,810,820 consists in adding an alcohol to the reaction mixture before, after or during the trimerization reaction, in order to obtain a polyisocyanate mixture comprising isocyanurate groups and allophanate groups. However, as above, the drawback of this method lies in a decrease in the functionality of the final polyisocyanate composition, in particular due to the presence of "true" allophanates, compounds composed of two monomer chains of isocyanates and of one allophanate functional group, the functionality of which is 2 in the case of diisocyanates, or of polyallophanates.

Thus, one aim of the present invention is to provide an optionally masked polyisocyanate composition of reduced viscosity having a high functionality of at least 3, preferably of greater than 3, in the case where it is obtained by polycondensation of diisocyanates, and an even higher functionality in the case of triisocyanates.

Another aim of the present invention is to provide an optionally masked polyisocyanate composition of reduced viscosity having a relatively low content of monouretidinedione polyisocyanates, and for which the degree of conversion of the starting monomers is greater than 35%.

Yet another aim of the present invention is to provide an optionally masked polyisocyanate composition of reduced viscosity having a reduced content of polyisocyanates comprising isocyanurate groups, especially of monoisocyanurate compounds, this content advantageously being not greater than 45% and preferably not greater than 40% by weight, relative to the weight of the isocyanates of the polyisocyanate composition.

These aims are achieved by virtue of the present invention, one subject of which is a polyisocyanate composition with a high mean functionality, obtained by polycondensation of diisocyanate or triisocyanate monomers, comprising:

(a) from 0.5% to 30% by mass, relative to the total mass of the components a), b) and c), of compounds bearing a single uretidinedione functional group having a molecular mass of not more than twice the average molecular mass of the isocyanate monomers having the highest molecular mass;

(b) from 0.5% to 45% by mass, relative to the total mass of the components a), b) and c), of compounds bearing a single isocyanurate functional group with a molecular mass of not more than three times the average molecular mass of the said isocyanate monomers having the highest molecular mass; the molar ratio of (a)/(b) being between 0.02 and 2, advantageously between 0.2 and 1.8, and preferably less than or equal to 1.6, (c) at least 40% by mass, relative to the total mass of the components a), b) and c), of a mixture of polyisocyanate compounds having a molecular mass at least equal to three times the average molecular mass of the isocyanate monomers having the smallest molecular mass and bearing at least two isocyanate functional groups, and said mixture comprising (i) compounds bearing at least two isocyanurate functional groups, excluding those comprising uretidinedione functions, (ii) compounds bearing at least two uretidinedione functional groups, excluding those comprising isocyanurate functions and for which the number of monomer units is less than 5, (iii) compounds bearing at least one isocyanurate functional group and at least one uretidinedione functional group, having a molecular mass greater than three times the highest molecular mass of the above isocyanate monomer compounds, said mixture having a ratio: carbonyl functional groups belonging to a uretidinedione ring/carbonyl functional groups belonging to an isocyanurate ring+carbonyl functional groups belonging to a uretidinedione ring, at least equal to 4%;

d) from 0 to 25% by mass, relative to the mass of the components a), b), c), d) and e), of compounds bearing at least one isocyanate functional group that are different than a), b) and c); and e) from 0 to 10% by mass, relative to the mass of the components a), b), c), d) and e), of impurities.

The term "high mean functionality" means a functionality of greater than 3, advantageously greater than 3.5 and preferably greater than 4.

It should be understood that there is no overlap between categories a) to e) defined above, and no overlap between categories (i), (ii) and (iii) defined above in c). This means that each of the components of the polyisocyanate composition belongs to one and only one of the categories defined in a), b), c)(i), c)(ii), c)(iii), d) and e). In other words, each component of the polyisocyanate composition according to the present invention is compatibilized only once in the calculations of the percentages of the various categories of components forming said polyisocyanate composition.

The expression "mean molecular mass of the isocyanate monomers having the highest (or lowest) molecular mass" means than when only one monomer is present, said "mean molecular mass" is equal to that of said sole monomer, when two different monomers are present, said "mean molecular mass" is equal to that of the monomer having the higher molecular mass (or the lower molecular mass, respectively), and that when three, or more, different monomers are present, said "mean molecular mass" is equal to the mean molecular mass of the two isocyanate monomers having the highest molecular mass (or the lowest molecular mass, respectively). As a general rule, not more than three different monomers are used in the context of the present invention.

For the purpose of the present invention, the term "reduced viscosity" is understood to mean that the viscosity, measured at 25° C. and expressed in mPa·s, is reduced by at least 10%, advantageously at least 12% and preferably at least 20%, relative to a known polyisocyanate composition obtained by cyclotrimerization of identical starting monomers and having the same functionality.

Generally, the polyisocyanate composition according to the present invention has a viscosity of between about 1 000 mPa·s and about 50 000 mPa·s, for a degree of conversion greater than 35%, preferably greater than 40%. For example, in the case where the starting monomer is HDI, the viscosity of a composition according to the invention is generally less than 25 000 mPa·s and advantageously less that 20 000 mPa·s, for a degree of conversion of the isocyanate functional groups of 37%, measured by quantitative determination with dibutylamine.

The component a) comprises the "monouretidinedione compounds", which are the condensation product of two isocyanate monomer molecules, also known as "true dimers", and advantageously represents from 1% to 30% by mass relative to the mass of the components a)+b)+c).

The component b) comprises the "monoisocyanurate compounds", which are the condensation product of three isocyanate monomer molecules, also known as "true trimers", and represents from 5% to 40% by mass relative to the mass of the components a)+b)+c).

In the mixture of compounds c), compounds (i) and (iii) have in common the fact that they are included in the category of "heavy fractions" bearing isocyanurate functions. Category b) comprises compounds bearing only one isocyanurate function. In the present invention, polyisocyanate compositions whose mass ratio [c)(i)+c)(iii)]/b)] is greater than 2, advantageously greater than 3 and preferably greater than 4 are also preferred. Specifically, it has been discovered, surprisingly, that the values of the ratio defined above are sufficient to obtain the high functionalities within the meaning of the present invention.

The mixture of compounds c) advantageously comprises:

polyisocyanate compounds containing two uretidinedione rings linked via one or more hydrocarbon-based chain(s);

polyisocyanate compounds containing two isocyanurate rings linked via one or more hydrocarbon-based chain(s).

The compounds comprising at least one uretidinedione ring and at least one isocyanurate ring forming part of the mixture c) advantageously comprise a group chosen from formulae (I) to (V) below, and mixtures thereof,

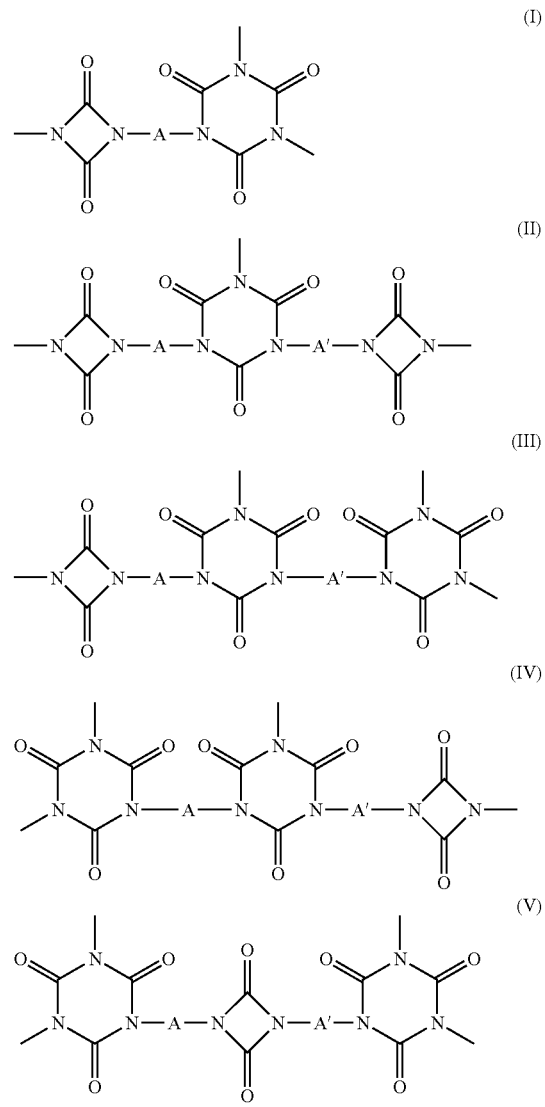

in which A and A', which may be identical or different, represent the residues of an isocyanate monomer compound after removal of two isocyanate functional groups.

Advantageously, A and A', which are identical, represent a divalent hydrocarbon-based chain comprising exclusively carbon and hydrogen atoms.

It is preferable for the composition c) to represent at least 45% and advantageously at least 50% by mass of the mass of the components a)+b)+c). Specifically, it is worthwhile recalling here that the higher the mass of compounds categorized in c), the more the number of isocyanate functions (i.e. the functionality) increases, with the proviso that the number of compounds categorized in c)(ii) is smaller than that of the other compounds categorized in c). To obtain a highest functionality, it is preferable for the amount of compounds c)(ii) to be less than 30% by weight relative to the total amount of compounds categorized in c), preferably less than 20% and more preferably less than 15%.

The increase in functionality is usually obtained, as in the case of the present invention, by increasing the degree of conversion. However, and as emerges from the prior art, this generally leads to a very substantial increase in viscosity. This phenomenon is observed to a less extent with the compositions of the present invention.

It is also expedient to recall here that the formation of a "heavy" compound comprising an isocyanurate unit increases the mean functionality of the composition by 1. Throughout the present invention, the functionality is expressed by mass, as is used in this field, that is to say the functional group of each element is weighted as a percentage relative to its proportion by mass.

As has been stated previously, the compositions of the present invention have a high functionality, that is to say a mean functionality greater than 3, advantageously greater than 3.5, preferably greater than 4, without however having a viscosity as high as that described in the prior art for polyisocyanate compositions having such a functionality.

According to one advantageous embodiment of the invention, the component d) represents not more than 10% by mass of the total mass of the components a)+b)+c)+d)+e), and represents not more than 5% by mass of the mass of the components a)+b)+c)+d)+e).

According to one advantageous embodiment of the invention, the component e) represents from 0.05% to 10%, generally from 0.1% to 8%, especially not more than 5% by mass relative to the total mass of the components a)+b)+c)+d)+e). Needless to say, the constituents of e) are inert with respect to the isocyanate functional groups present in a), b), c) or d).

The component e) generally consists of compounds not bearing free isocyanate functional groups, and especially consists of residues formed from polycondensation catalysts and/or of byproducts from the polycondensation of the starting isocyanate monomers and/or of solvents.

The component d) comprises said starting isocyanate monomer or monomers, which advantageously represent from 0.05% to 20%, more generally from 0.1% to 10%, advantageously not more than 2% and preferably not more than 1% by mass of the total mass of the components of the total mass of a)+b)+c)+d)+e).

The composition d) also comprises isocyanate compounds, advantageously isocyanate monomer compounds, optionally added after the polycondensation reaction of the diisocyanate monomers, such as isocyanates or triisocyanates of low molecular weight (not more than 500), for example a lysine triisocyanate.

Another subject of the invention is a composition as defined above also comprising an amount of not more than 200%, advantageously not more than 100% and preferably not more than 50% by mass, relative to the components a), b), c), d) and e), of an organic solvent or a mixture of organic solvents.

The organic solvent or the mixture of organic solvents is generally liquid at ambient temperature, does not comprise an isocyanate functional group and does not comprise a functional group capable of reacting with the isocyanate functional group, has a boiling point of not more than 300° C., advantageously 250° C. and preferably not more than 200° C., and is miscible with the components a), b), c) and d). It is also advisable for the melting point of said solvent (the term solvent also means the mixtures of solvents) to be not higher than ambient temperature, advantageously 0° C.; in the case of mixtures, the melting points are not sharp (with the exception, of course, of eutectic mixtures) and, in this case, the above values refer to the end melting point.

Another subject of the invention is a polyisocyanate composition as defined above comprising from 1% to 100% and advantageously from 10% to 100% of the NCO groups present in the composition that have reacted with a compound comprising a labile hydrogen. Some of the compounds comprising a labile hydrogen are known as "masking agents" insofar as they can result in the restoration of the isocyanate functional group via a thermal or physicochemical process. These masking agents generally restore the isocyanate functional group between 50 and 200° C. over a time of between 5 minutes and one hour.

Preferably, the polyisocyanate compounds of the composition of the invention are the condensation product of two, three or more than three isocyanate molecules bearing two or three isocyanate functional groups, denoted in the present description as diisocyanate monomers or triisocyanate monomers.

They may be isocyanate monomers comprising a linear, branched or cyclic hydrocarbon-based backbone exclusively of aliphatic nature or may be aromatic isocyanates.

A linear aliphatic monomer that may be mentioned in particular is hexamethylene diisocyanate (HDI). Mention may also be made of aliphatic monomers, the hydrocarbon-based backbone of which is branched but the isocyanate functional groups of which are borne by primary carbon atoms, for example 2-methylpentane diisocyanate. Mention may also be made of the monomers, at least one isocyanate functional group of which is in the secondary, tertiary or neopentyl cycloaliphatic position.

They are in particular monomers in which the isocyanate functional group is borne by a secondary, tertiary or neopentyl cycloaliphatic carbon atom, in particular cycloaliphatic isocyanates. These monomers are such that advantageously at least one of the two isocyanate functional groups is distant from the closest ring by not more than one carbon and is preferably directly attached thereto. In addition, these cycloaliphatic monomers advantageously contain at least one and preferably two isocyanate functional groups chosen from secondary, tertiary and neopentyl isocyanate functional groups.

Examples of monomers that may be mentioned include the following:

compounds corresponding to the hydrogenation of the aromatic nucleus or nuclei bearing isocyanate functional groups of aromatic isocyanate monomers and in particular of TDI (toluene diisocyanate) and of diisocyanatobiphenyls, the compound known under the abbreviation $H_{12}MDI$ (4,4'-bis(isocyanatocyclohexyl)methane), various BIC [bis(isocyanatomethylcyclohexane)] compounds and cyclohexyl diisocyanates, optionally substituted;

and especially norbornane diisocyanate, often denoted by its abbreviation NBDI;

isophorone diisocyanate or IPDI or more specifically 3-isocyanatomethyl-3,5,5-trimethylcyclohexyl isocyanate.

Aromatic monomers that may be mentioned include:

2,4- or 2,6-toluene diisocyanate (TDI);

2,6-(4,4'-diphenylmethane) diisocyanate (MDI);

1,5-naphthalene diisocyanate (NDI);

para-phenylene diisocyanate (PPDI).

Preference is given to aliphatic isocyanate monomers, including cycloaliphatic isocyanate monomers, the preferred ones being aliphatic isocyanate monomers comprising polymethylene linkages. The term "aliphatic isocyanate monomer" is understood to mean monomers, at least one isocyanate functional group of which is attached to a carbon atom of $sp^3$ hybridization; advantageously two isocyanate functional groups and preferably all the isocyanate functional groups are attached to carbon atoms of $sp^3$ hybridization.

The starting isocyanate monomers of low molecular mass as defined above generally have a content of isocyanate groups of at least 12%, preferably at least 15% and preferentially at least 20%, expressed by weight of NCO relative to the total weight of isocyanate.

The starting monomers can also be oligomerization products of isocyanates of low molecular mass as defined above, these oligomerization products bearing masked or nonmasked isocyanate functional groups.

The masking group is the consequence of the reaction of a compound containing at least one reactive hydrogen atom with the isocyanate functional group of the polyisocyanates as defined above.

The masking agent, which may be a mixture of masking agents, is such that the masking reaction can be written:

where MA-H represents the masking agent;
where MA- represents the masking group;
where Is is the residue bearing the isocyanate functional group under consideration.

Said masking agent contains at least one functional group bearing a labile hydrogen or more exactly a reactive hydrogen, for which functional group it is possible to define a pKa that corresponds either to the ionization of an acid, including the hydrogen of the phenol and alcohol functional groups, or to the associated acid of a base, generally a nitrogenous base. The pKa of the functional group containing hydrogens is at least equal to 4, advantageously to 5 and preferably to 6, and is not more than 14, advantageously 13, preferably 12 and more preferably 10, an exception having to be made for lactams, the pKa of which is greater than these values, which constitute masking agents that are nevertheless acceptable although not preferred for the invention.

The masking agent advantageously comprises only one labile hydrogen.

Nonlimiting examples of masking agents according to the invention that may be mentioned include hydroxylamine derivatives, such as hydroxysuccinimide, and oximes, such as methyl ethyl ketoxime or methyl pyruvate oxime, phenol derivatives or comparable compounds, amide derivatives, such as imides and lactams, and also malonates or keto esters and hydroxamates.

Mention may also be made of nitrogenous heterocyclic groups containing 2 to 9 carbon atoms and, in addition to the nitrogen atom, from 1 to 3 other heteroatoms chosen from nitrogen, oxygen and sulfur. These groups are chosen, for example, from pyrrolyl, 2H-pyrrolyl, imidazolyl, pyrimidinyl, pyridazinyl, pyrazinyl, pyrimidinyl, pyridazinyl, indolizinyl, isoindolyl, indolyl, indozolyl, purinyl, quinolizinyl, isoquinolyl, pyrazolidinyl, imidazolidinyl and triazolyl groups. Preference is given in particular to heterocycles containing from 2 to 4 carbon atoms and from 1 to 3 nitrogen atoms, such as pyrazolyl, imidazolyl and triazolyl groups, these groups optionally being substituted with one to three substituents chosen from $NH_2$, $NH(C_1$–$C_6$ alkyl), N-(di $(C_1$–$C_6$ alkyl)), OH, SH, $CF_3$, $C_1$–$C_6$ alkyl, $C_3$–$C_6$ cycloalkyl, $C_5$–$C_{12}$ aryl, in particular phenyl, $C_6$–$C_{18}$ aralkyl containing from 5 to 12 carbon atoms in the aryl group, in particular benzyl, and $C_6$–$C_{18}$ alkaryl containing from 5 to 12 carbon atoms in the aryl group.

The 1,2,3-triazolyl, 1,2,4-triazolyl and 3,5-dimethylpyrazolyl groups are particularly preferred.

Reference may be made, for the determination of the pKa values, to "The determination of ionization constants, a laboratory manual, A. Albert of E. P. Serjeant; Chapman and Hall Ltd, London".

Reference may be made, for the list of masking agents, to Z. Wicks (*Prog. Org. Chem.*, (1975), 3, 73 and *Prog. Org. Chem.*, (1989), 9, 7) and Petersen (Justus Liebigs, *Annalen der Chemie*, 562, 205, (1949).

The organic solvent is advantageously chosen from:
aromatic hydrocarbons, in particular toluene, xylene or Solvesso®;
esters, such as n-butyl acetate, dimethyl adipate, methyl glutarate, or their mixtures;
ether esters, such as methoxypropyl acetate;
ethers, such as butyl glycol ether;
ketones, such as methyl isobutyl ketone;
fluorinated solvents, such as trifluoromethylbenzene.

The polyisocyanate composition according to the invention may be obtained by a process comprising the following steps:
 i) a starting reaction medium is prepared comprising the starting isocyanate monomer(s) and optionally other monomers that react with the isocyanate functional group;
 ii) the starting reaction medium is reacted in the presence of a dimerization catalyst, optionally by heating the reaction medium to a temperature of at least 40° C.;
 iii) the reaction product from step ii), comprising unreacted monomers, is reacted with a (cyclo)trimerization catalyst under (cyclo)trimerization conditions;
 iv) the unreacted starting monomers are removed from the reaction product from step iii);
 in which process step iii) is carried out until a degree of conversion of the isocyanate monomers present in the starting reaction medium of at least 35%, advantageously of at least 40% is achieved.

The residual level of monomers is measured by quantitative determination after separation of the polyisocyanate mixture on a separating column of gel filtration chromatography type in a solvent such as dichloromethane ($CH_2Cl_2$) or tetrahydrofuran (THF). The detection method is infrared spectroscopy, the NCO band at 2250 $cm^{-1}$ being measured after calibration with a monomer of known concentration.

As a variant, the polyisocyanate composition according to the invention may also be obtained by a process comprising the following steps:
 i) a starting reaction medium is prepared comprising the starting isocyanate monomer(s) and optionally other monomers that react with the isocyanate functional group;
 ii) the starting monomers are reacted with a (cyclo) trimerization catalyst under (cyclo)trimerization conditions;
 iii) the medium of step ii) is reacted in the presence of a dimerization catalyst, optionally by heating the reaction medium to a temperature of at least 40° C.;
 iv) the unreacted starting monomers are removed from the reaction product from step iii);
 in which process step iii) is carried out until a degree of conversion of the isocyanate monomers present in the starting reaction medium of at least 35%, advantageously of at least 40% is achieved.

The reaction can be carried out in the absence or presence of a solvent. It is generally preferable to carry it out in the absence of solvent.

It is also possible, in accordance with the process of the invention, to prepare the polyisocyanate composition continuously, by withdrawing the unreacted starting monomers and by recycling them in the polycondensation step.

The compounds a), b) and c) according to the invention can be obtained from a single monomer or a mixture of different monomers.

The reaction for the formation of the uretidinedione compounds can be carried out exclusively via a catalytic route, in the absence of heating. This catalytic dimerization in the absence of heating is one of the advantageous embodiments according to the present invention. These specific catalysts are those that are known to a person skilled in the art as giving uretidinediones from isocyanate functional groups, this being achieved with little or no other type of condensation (in particular formation of isocyanurate). A few illustrative examples of such catalysts specific for dimerization are given below.

Thus, the catalysts specific for dimerization are those that are known to a person skilled in the art for forming uretidinedione groups from isocyanate functional groups and are chosen from compounds of tris(N,N-dialkyl)phosphotriamide or N,N-dialkylaminopyridine type or of trialkylphosphine type. A most particularly preferred example of dimerization catalysts for the production of the compositions according to the invention is represented by catalysts of trialkylphosphine type.

According to one variant, it may be advantageous to heat the reaction medium during the reaction for the formation of the uretidinedione compounds via a catalytic route. The dimerization reaction is then carried out via the catalytic and thermal route. It should also be noted that with certain catalysts, such as trialkylphosphines, the increase in temperature promotes the trimerization reaction.

Some catalysts, such as those of tris(N,N-dialkyl)phosphotriamide and N,N-dialkylaminopyridine type, result in the specific formation of dimers as highly predominant products. When such "dimerization" catalysts are used, it may be advantageous to add a trimerization catalyst, so as to carry out the dimerization and trimerization reactions in conjunction.

In addition, some catalysts enable both dimerization and trimerization reactions. An example of these catalysts is represented by those of trialkylphosphine type.

The novelty of the catalytic dimerization process in the present invention lies in the fact that, although the catalytic dimerization reactions are known per se, this catalytic dimerization is performed until degrees of conversion of the starting monomer and/or oligomer species of greater than 35%, advantageously greater than 40%, or even higher than these limits, are obtained.

This formation of uretidinedione rings is especially performed in the presence of compounds such as trialkylphosphines, tris(N,N-dialkyl)phosphotriamides and N,N,N',N'-tetraalkylguanidines.

The cyclotrimerization catalyst can be any catalyst known for this purpose. Mention may be made of tertiary amines, such as triethylamine, Mannich bases, such as tris(N,N-dimethylaminomethyl)phenol, hydroxides or salts of weak organic acids or fluorides of tetraalkylammoniums, such as tetramethyl-, tetraethyl- and tetrabutylammoniums, hydroxides and salts of weak organic acids of hydroxyalkylammoniums, such as N,N,N-trimethyl-N-hydroxyethylammonium carboxylate or N,N,N-trimethyl-N-hydroxypropylammonium hydroxide; alkali metal, alkaline-earth metal, tin, zinc or other metal salts of carboxylic acids, such as acetic, propionic, octanoic or benzoic acid, or carbonates of these metals; alkoxides or phenoxides of alkali metals, alkaline-earth metals, tin, zinc or other metals; tertiary alkylphosphines, such as disclosed in U.S. Pat. No. 3,211,703, the compounds of heavy metals, such as iron acetylacetonate, disclosed in U.S. Pat. No. 3,135,111, the silylamines and hexamethyldisilazane disclosed in EP 89297; or the alkoxides of rare-earth metals disclosed in FR 99 16 687.

On conclusion of the cyclotrimerization reaction, the cyclotrimerization catalyst is deactivated by any known means, in particular by addition of a catalyst poison or by absorption on an alumina column.

In the case where the catalytic cyclodimerization step is carried out after the cyclotrimerization reaction, it is advisable to ensure that the trimerization catalyst has indeed been deactivated.

In general, when a dimerization and/or trimerization catalyst is used in the processes as have just been described, it should be understood that the polyisocyanate compositions according to the present invention may also contain traces of these catalysts or of derivatives thereof derived from their decomposition.

When it is desired to obtain a masked polyisocyanate composition as defined above, the isocyanate functional groups present in the reaction medium are reacted with the masking agent before, during or after the steps described above.

However, it is preferable to carry out the masking reaction after the polycondensation reaction and after removal of the unreacted isocyanate monomers.

One of the many advantages of the polyisocyanate compositions according to the invention is that they can act as base for preparing polymers and/or crosslinked materials and can be used in particular as one of the main constituents of coatings of all types, such as varnishes and paints. In such uses, the hardness qualities of the crosslinkable polymers are among those that are desired technically and functionally.

The process for preparing polymers comprises the following steps:

bringing a polyisocyanate composition according to the invention into contact with a coreactant which comprises derivatives containing reactive hydrogens in the form of alcohol, of phenol, of thiol or of certain amines, including anilines; these derivatives can have linear or branched and substituted or unsubstituted aliphatic, alicyclic or aromatic hydrocarbon-based backbones, preferably alkyl, including cycloalkyl and aralkyl, or aryl backbones (these coreactants, generally polyols, are known per se) and form, after reaction with the polyisocyanates, a network;

and heating the reaction medium thus formed to a temperature that allows crosslinking of the components.

Advantageously, the temperature is not more than about 300° C., preferably at least equal to 60° C., preferentially at least equal to 80° C. and preferably not more than 250° C. and more preferably still 200° C., for a period of time of less than or equal to 15 hours, preferably of less than or equal to 10 hours and more preferably still less than or equal to 8 hours. It is known to a person skilled in the art that the higher the temperature, the less time needed to carry out the crosslinking by curing. Thus, curing at 300° C. requires only a few tens of seconds, indeed even a few minutes, whereas a temperature of 60° C. requires a time that is expressed in hours.

Provision may be made to include an organic solvent in the crosslinking reaction medium. Provision may also be made for a suspension in water.

This optional solvent is preferably of low polarity, i.e. its dielectric constant is barely greater than or equal to 4 or more preferably greater than or equal to 5.

In accordance with the invention, the preferred low-polarity solvents are those that are well known to a person skilled in the art and in particular aromatic solvents, such as benzene, ketones, such as cyclohexanone, methyl ethyl ketone and acetone; light alkyl esters and in particular adipic esters; or petroleum fractions of the type sold under the trade name Solvesso®.

Generally, the solvent is identical to the solvent of the above polyisocyanate composition.

The derivatives forming part of the composition of the coreactant are generally di-, oligo- or polyfunctional derivatives, can be monomers or can result from di-, oligo- or polymerization, and are employed in the preparation of optionally crosslinked polyurethanes; their choice will be dictated by the functionalities expected for the polymer in the final application and by their reactivity.

In particular when it is desired to have stable "two-component" compositions (i.e. simultaneously comprising the two reactants: the polyisocyanate composition, in this instance at least partially masked, according to the invention and the compound comprising reactive hydrogen), it is preferable to avoid the use of derivatives containing reactive hydrogens that catalyze the release of the masked isocyanate. Thus, among amines, it is preferable to use only those that do not catalyze the decomposition or the transamidation of the masked isocyanate functional groups according to the present invention. These coreactants are generally well known to a person skilled in the art.

The invention thus also relates to paint compositions comprising, for successive or simultaneous addition:
 a masked polyisocyanate according to the invention;
 a coreactant comprising reactive hydrogen as described above;
 optional catalysts known per se (in particular those based on tin for oximes);
 optionally at least one pigment, such as titanium dioxide;
 optionally an aqueous phase;
 optionally a surfactant to keep the constituent components of the mixture in emulsion or in suspension;
 optionally an organic solvent;
 optionally a dehydrating agent.

The catalysts are advantageously latent, in particular those that have formed the subject of patent and of patent application published on behalf of the Applicant Company or of its predecessors in law (company comprising "Rhône-Poulenc" in its name).

The invention also relates to paints and varnishes obtained by the use of these compositions, according to the above process.

The examples that follow illustrate the invention.
Abbreviations used:
HMDZ: hexamethyldisilazane
HDI: hexamethylene diisocyanate
AcO(n-butyl): n-butyl acetate
NCO functional group: isocyanate functional group
MEKO: butanone or methyl ethyl ketoxime
DMP: 3,5-dimethylpyrazole
poly NCO: polyisocyanate The amounts of the various components presented in the present description, examples and claims are expressed as percentage by mass, unless otherwise indicated.

The meaning of the usual vernacular terms is recalled below:
 bis-dimer: oligomer derived from the condensation of three monomers and containing two uretidinedione units;
 tris-dimer: tetramer containing three uretidinedione units;
 bis-trimer: pentamer containing two isocyanurate units;
 trimer-dimer: tetramer containing one isocyanurate unit and one uretidinedione unit;
 trimer-dimer-trimer: hexamer containing two isocyanurate units and one uretidinedione unit.

The "heavy fractions" correspond to oligomers with a molecular mass greater than or equal to 7 times that of the monomers.

It is recalled that, according to the usual technique of the art, the various components of the oligomer fraction are identified by infrared structural analysis, their distributions and their functionalities are given and quantified using the characteristic bands of the polyisocyanate compounds, i.e. the bands of the isocyanate functions, the alkyl bands, the CO bands of the isocyanurate and those of the uretidinedione. The oligomeric distribution by weight corresponding to each illustrated synthesis is thus obtained.

For each oligomer and each oligomer fraction there is a corresponding functionality measured (by the content of NCO functional group), which, in the case of pure oligomers, may be compared with the theory (thus, the HDI dimer has a functionality of 2).

It is recalled that in the field, the functionality is obtained in the following manner: the weight percentage of each oligomer of the composition is multiplied by its intrinsic functionality and the functionalities provided by each oligomer are then totaled. The total represents the mean functionality of the oligomer composition. In the case of the present invention, the final compositions are subjected to separation on a set of gel permeation columns sold by the company Polymer Laboratories under the brand name PL Gel mixed type E.

The NCO titer is measured, in the usual manner, according to AFNOR standard NF T 52-132 of September 1988 (occasionally referred to as the dibutylamine method).

The viscosity is measured, in the usual manner, according to standard NF EN ISO 3219 of November 1994 (Method for determination of viscosity by the rotating drum method).

Examples 1 and 2 below are representative of polyisocyanates of low viscosity and high functionality using tributylphosphine as catalyst.

EXAMPLE 1

310 g of HDI are added under nitrogen to a three-necked reactor equipped with a mechanical stirrer, a condenser and an addition funnel. The reaction medium is degassed by bubbling nitrogen through for 1 hour and 1.18 g of tri-n-butylphosphine are then added under nitrogen. The reaction medium is heated at 60° C. for about 10 hours.

When the degree of conversion of NCO functional groups, measured according to the dibutylamine method, is 39.6% (which corresponds to a theoretical degree of conversion of HDI of 79.2%), the reaction is quenched by addition of one molar equivalent of methyl tosylate relative to the catalyst introduced. This degree of conversion of 39.6% corresponds to a degree of conversion of HDI of 63.1% measured on the reaction mixture before removal of the HDI monomer according to the gel permeation chromatography technique. The reaction medium is stirred for 2 hours at 80° C.

The product is purified by distilling off the unconverted HDI monomer, under a vacuum of 0.4 mbar, at 160° C., on a thin-film machine, at a flow rate of about 200 g/hour. This operation is repeated a second time to give 162 g of HDI oligomerization product, i.e. a recovered yield of 52%.

The characteristics of the product are as follows:
Degree of conversion: 63%
NCO titer of the reaction mixture after distillation: 18.7%
Viscosity of the reaction mixture at 25° C.: 1043 mPa·s.

Functionality: about 3.5.

The composition of the mixture obtained, after removal of the HDI monomer, is given in the table below.

| Category | Compound | Functionality | Weight % | Contribution to the functionality |
|---|---|---|---|---|
| | HDI (starting monomer) | 2 | 1 | 0.02 |
| a) | HDI uretidinedione (HDI dimer) | 2 | 24 | 0.48 |
| b) | Trimer | 3 | 15 | 0.45 |
| c)(ii) | Bis-dimer | 2 | 8 | 0.16 |
| c)(iii) | Trimer-dimer | 3 | 10 | 0.3 |
| c)(ii) | Tris-dimer | 2 | 4 | 0.08 |
| c)(i) and (iii) | Bis-trimer + (trimer-dimer-trimer) | 4 | 12 | 0.48 |
| c)(i) and (iii) | Heavy fractions | ~5.8 | 26 | 1.51 |

The ratio of true dimer to the sum (true dimer+true trimer) is 0.61.

The ratio C=O dimer/C=O (dimer+trimer) measured on the overall distribution is 43%.

The heavy compounds consist of sequences as defined in the invention, i.e. sequences of trimer-dimer, trimer-trimer-dimer, trimer-dimer-trimer, etc. blocks.

The ratio of the compounds [(trimer-dimer)+(tris-dimer)+(bis-trimer)+(trimer-dimer-trimer)+heavy fractions] to the Trimer compounds, i.e. the ratio [(c)(i)+c)(iii))/b)] is about 3.5.

EXAMPLE 2

The process is performed as for the preceding example, except that the amount of tri-n-butylphosphine is 2.25 g and the degree of conversion of HDI measured after gel permeation chromatography is 85.6%.

The functionality is about 5.

The distribution of the species before distillation of the monomer is as follows:

| Category | Compound | Functionality | Weight % | Contribution to the functionality |
|---|---|---|---|---|
| | HDI (starting monomer) | 2 | 14.4 | ‡ |
| a) | HDI uretidinedione (HDI dimer) | 2 | 5 | 0.116 |
| b) | Trimer | 3 | 7 | 0.245 |
| c)(ii) | Bis-dimer | 2 | 1.2 | 0.028 |
| c)(iii) | Trimer-dimer | 3 | 3.3 | 0.115 |
| c)(ii) | Tris-dimer | 2 | 1.1 | 0.025 |
| c)(i) and (iii) | Bis-trimer + (trimer-dimer-trimer) | 4 | 6.3 | 0.294 |
| c)(i) and (iii) | Heavy fractions | ~6 | 61.7 | 4.32 |

‡: not taken into account in the calculation of the total functionality of the composition The heavy compounds consist of sequences as defined in the invention, i.e. sequences of trimer-dimer, trimer-trimer-dimer, trimer-dimer-trimer, etc. blocks.

The ratio of the compounds [(trimer-dimer)+(tris-dimer)+(bis-trimer)+(trimer-dimer-trimer)+heavy fractions] to the Trimer compounds, i.e. the ratio [(c)(i)+c)(iii))/b)] is about 10.

The distribution between the dimer and trimer functions is as follows:

| | % trimer C=O functions | % dimer C=O functions | Ratio C=O dimer/ C=O (trimer + dimer) |
|---|---|---|---|
| Overall distribution | 69.1% | 30.9% | 30.9% |
| Heavy fractions | 56.2% | 21.7% | 27.9% |
| Bis species* | 6.9% | 4.2% | 37.9% |
| True species** | 6% | 5% | 45.3% |

*The term "bis species" means the bis dimer and the bis trimer
**The term "true species" means the dimer (component a)) and the cyclotrimer (component b)).

The invention claimed is:

1. A polyisocyanate composition with a high mean functionality, obtained by polycondensation of diisocyanate or triisocyanate monomers, comprising:
   (a) from 0.5% to 30% by mass, relative to the total mass of the components a), b) and c), of compounds bearing a single uretidinedione functional group having a molecular mass of not more than twice the average molecular mass of the isocyanate monomers having the highest molecular mass;
   (b) from 0.5% to 45% by mass, relative to the total mass of the components a), b) and c), of compounds bearing a single isocyanurate functional group with a molecular mass of not more than three times the average molecular mass of said isocyanate monomers having the highest molecular mass;
   the molar ratio of (a)/(b) being between 0.02 and 2,
   (c) at least 40% by mass, relative to the total mass of the components a), b) and c), of a mixture of polyisocyanate compounds having a molecular mass at least equal to three times the average molecular mass of the isocyanate monomers having the smallest molecular mass and bearing at least two isocyanate functional groups, and
   said mixture comprising
   (i) compounds bearing at least two isocyanurate functional groups, excluding those comprising uretidinedione functions,
   (ii) compounds bearing at least two uretidinedione functional groups, excluding those comprising isocyanurate functions and for which the number of monomer units is less than 5,
   (iii) compounds bearing at least one isocyanurate functional group and at least one uretidinedione functional group, having a molecular mass greater than three times the highest molecular mass of the above isocyanate monomer compounds;
   said mixture having a ratio: carbonyl functional groups belonging to a uretidinedione ring/carbonyl functional groups belonging to an isocyanurate ring+carbonyl functional groups belonging to a uretidinedione ring, at least equal to 4%;
   d) from 0 to 25% by mass, relative to the mass of the components a), b), c), d) and e), of compounds bearing at least one isocyanate functional group that are different than a), b) and c); and
   e) from 0 to 10% by mass, relative to the mass of the components a), b), c), d) and e), of impurities;
   said polysocyanate composition having a functional of greater than 3.

2. A polyisocyanate composition with a high mean functionality, obtained by polycondensation of diisocyanate or triisocyanate monomers, comprising:

(a) from 0.5% to 30% by mass, relative to the total mass of the components a), b) and c), of compounds bearing a single uretidinedione functional group having a molecular mass of not more than twice the average molecular mass of the isocyanate monomers having the highest molecular mass;

(b) from 0.5% to 45% by mass, relative to the total mass of the components a), b) and c), of compounds bearing a single isocyanurate functional group with a molecular mass of not more than three times the average molecular mass of said isocyanate monomers having the highest molecular mass;

the molar ratio of (a)/(b) being between 0.02 and 2, (c) at least 40% by mass, relative to the total mass of the components a), b) and c), of a mixture of polyisocyanate compounds having a molecular mass at least equal to three times the average molecular mass of the isocyanate monomers having the smallest molecular mass and bearing at least two isocyanate functional groups, and said mixture comprising (i) compounds bearing at least two isocyanurate functional groups, excluding those comprising uretidinedione functions, (ii) compounds bearing at least two uretidinedione functional groups, excluding those comprising isocyanurate functions and for which the number of monomer units is less than 5, (iii) compounds bearing at least one isocyanurate functional group and at least one uretidinedione functional group, having a molecular mass greater than three times the highest molecular mass of the above isocyanate monomer compounds;

said mixture having a ratio: carbonyl functional groups belonging to a uretidinedione ring/carbonyl functional groups belonging to an isocyanurate ring+carbonyl functional groups belonging to a uretidinedione ring, at least equal to 4%;

d) from 0 to 25% by mass, relative to the mass of the components a), b), c), d) and e), of compounds bearing at least one isocyanate functional group that are different than a), b) and c); and e) from 0 to 10% by mass, relative to the mass of the components a), b), c), d) and e), of impurities;

said polyisocyanate composition having a functionality of greater than 3.5.

3. The polyisocyanate composition as claimed in claim 1, comprising from 1% to 30% by mass of the component (a) relative to the total mass of the components a)+b)+c).

4. The polyisocyanate composition as claimed in claim 1, comprising from 5% to 40% by mass of the component (b) relative to the total mass of the components a)+b)+c).

5. The polyisocyanate composition as claimed in claim 1, wherein the component c) represents at least 45% by mass relative to the total mass of the components a)+b)+c).

6. A polyisocyanate composition with a high mean functionality, obtained by polycondensation diisocyanate or tri-isocyanate monomers, comprising:

(a) from 0.5% to 30% by mass, relative to the total mass of the components a), b) and c), of compounds bearing a single uretidinedione functional group having a molecular mass of not more than twice the average molecular mass of the isocyanate monomers having the highest molecular mass;

(b) from 0.5% to 45% by mass, relative to the total mass of the components a), b) and c), of components bearings a single isocyanurate functional group with a molecular mass of not more than three times the average molecular mass of said isocyanate monomers having the highest molecular mass;

the molar ratio of (a)/(b) being between 0.02 and 2, (c) at least 40% by mass, relative to the mass of the components a), b) and c), of a mixture of polyisocyanate compounds having a molecular mass at least equal to three times the average molecular mass of the isocyanate monomers having the smallest molecular mass and bearing at least two isocyanate functional groups, and said mixture comprising (i) compounds bearing at least two isocyanurate functional groups, excluding those comprising uretidinedione functions, (ii) compounds bearing at least two uretidinedione functional groups, excluding those comprising isocyanurate functions and for which the number of monomer units is less than 5, (iii) compounds bearing at least two isocyanurate functional group and at least one uretidinedione functional group, having a molecular mass greater than three times the highest molecular mass of the above isocyanate monomer compounds:

said mixture having a ratio: carbonyl functional groups to a uretidinedione ring/carbonyl functional groups belonging to an isocyanurate ring+carbonyl functional groups belonging to a uretidinedione ring, at least equal to 4%;

d) from 0 to 25% by mass, relative to the mass of the components a), b), c), d) and e), of compounds bearing at least one isocyanurate functional group that are different than a), b) and c); and e) from 0 to 10% by mass, relative to the mass of the components a), b), c), d) and e), of impurities;

said polyisocyanate composition having a functionally of greater than 3, wherein the mass ratio [c)(i)+c)(iii)]/b) is greater than 2.

7. The polyisocyanate composition as claimed in claim 1, wherein the amount of compounds c)(ii) is less than 30% by weight relative to the total amount of compounds categorized in c).

8. The polyisocyanate composition as claimed in claim 1, wherein the component d) represents not more than 10% by mass relative to the total mass of the components a)+b)+c)+d)+e).

9. The polyisocyanate composition as claimed in claim 1, wherein the component e) represents from 0.05% to 10% by mass relative to the total mass of the components a)+b)+c)+d)+e).

10. The polyisocyanate composition as claimed in claim 1, wherein the component e) consists of residues formed from polycondensation catalyst and/or of byproducts from the polycondensation of the starting isocyanate monomers and/or of solvent(s).

11. The polyisocyanate composition as claimed in claim 1, wherein the component d) comprises said residual isocyanate monomer(s).

12. The polyisocyanate composition as claimed in claim 11, wherein said isocyanate monomer(s) represent(s) from 0.05% to 20% by mass of the mass of the components a)+b)+c)+d)+e).

13. The composition as claimed in claim 1, further comprising an amount of not more than 200% by mass of a)+b)+c)+d)+e), of an organic solvent or mixture of organic solvents that is liquid at ambient temperature, which does not comprise an isocyanate functional group, which does not comprise a functional group capable of reacting with the isocyanate functional group, which has a boiling point of not more than 200° C. and which is miscible with the components a), b), c), d) and e).

14. The composition as claimed in claim 1, wherein the compounds comprising at least one uretidinedione ring and at least one isocyanurate ring comprise a group chosen from formulae (I) to (V) below, and mixtures thereof:

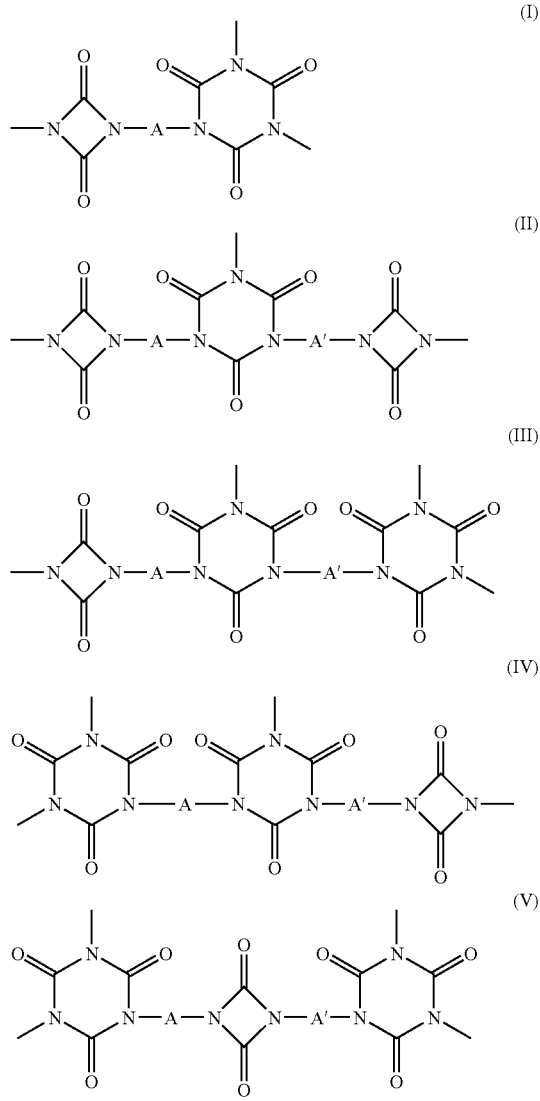

in which A and A', which may be identical or different, represent the residues of an isocyanate monomer compound after removal of two isocyanate functional groups.

15. The composition as claimed in claim 1, comprising from 1% to 100% of the NCO groups present in the composition masked using a masking agent.

16. The composition as claimed in claim 15, wherein the masking agent is a monofunctional masking agent selected from the group consisting of hydroxylamine derivatives, oximes, phenol derivatives, amide derivatives, malonates, keto esters, hydroxamates and nitrogenous heterocyclic compounds.

17. The composition as claimed in claim 16, wherein the masking agent is methyl ethyl ketoxime or methyl pyruvate oxime.

18. The composition as claimed in claim 15, wherein the masking agent is chosen from pyrrolyl, 2H-pyrrolyl, imidazolyl, pyrimidinyl, pyridazinyl, pyrazinyl, pyrimidinyl, pyridazinyl, indolizinyl, isoindolyl, indolyl, indozolyl, purinyl, quinolizinyl, isoquinolyl, pyrazolidinyl, imidazolidinyl and triazolyl groups.

19. A process for preparing the polyisocyanate composition as claimed in claim 1, comprising the following steps:
   i) preparing a starting reaction medium comprising the starting isocyanate monomer(s) and optionally other monomers that react with the isocyanate functional group;
   ii) reacting the starting reaction medium in the presence of a dimerization catalyst, optionally by heating the reaction medium to a temperature of at least 40° C.;
   iii) reacting the reaction product from step ii), comprising unreacted monomers, with a (cyclo)trimerization catalyst under (cyclo)trimerization conditions;
   iv) removing the unreacted starting monomers are removed from the reaction product from step iii);
   v) optionally reacting the reaction medium with a masking agent before, during or after steps i) to iv);
   process step iii) is carried out until a degree of conversion of isocyanate monomers present in the starting reaction medium of at least 35% is achieved.

20. A process for preparing the polyisocyanate composition as claimed in claim 1, comprising the following steps:
   i) preparing a starting reaction medium comprising the starting isocyanate monomer(s) and optionally other monomers that react with the isocyanate functional group;
   ii) reacting the starting monomers with a (cyclo)trimerization catalyst under (cyclo)trimerization conditions;
   iii) reacting the reaction medium of step ii) in the presence of a dimerization catalyst, optionally by heating the reaction medium to a temperature of at least 40° C.;
   iv) reacting the unreacted starting monomers are removed from the reaction product from step iii); and
   v) optionally reacting the reaction medium with a masking agent before, during or after steps i) to iv);
   process step iii) is carried out until a degree of conversion of isocyanate monomers present in the starting reaction medium of at least 35% is achieved.

21. The process as claimed in claim 19, wherein the dimerization catalyst is selected from the group consisting of tris(N,N-dialkyl)phosphotriamides, N,N-dialkylaminopyridines and trialkylphosphines.

22. The process as claimed in claim 19, wherein the dimerization catalyst is a trialkylphosphine.

23. The process as claimed in claim 19, wherein the trimerization catalyst is a trialkylphosphine.

24. The composition as claimed in claim 1, for preparing a coating, further comprising, for successive or simultaneous addition, a coreactant comprising reactive hydrogen.

25. A method for preparing a paint or other coating comprising incorporating therein a composition as claimed in claim 1.

26. A process for preparing polymers, comprising the following steps:
   bringing the polyisocyanate composition as defined in claim 1 into contact with a coreactant that comprises derivatives containing reactive hydrogens; and
   heating the reaction medium thus formed to a temperature that allows crosslinking of the components.

27. The polysocyanate composition as claimed in claim 1, wherein the molar ratio of (a)/(b) being between 0.02 and 1.8.

28. The polysocyanate composition as claimed in claim 27, wherein the molar ratio of (a)/(b) is less than or equal to 1.6.

29. A polyisocyanate composition with a high mean functionality, obtained by polycondensation of diisocyanate or triisocyanate monomers, comprising:
   (a) from 0.5% to 30% by mass, relative to the total mass of the components a), b) and c), of compounds bearing a single uretidinedione functional group having a molecular mass of not more than twice the average molecular mass of the isocyanate monomers having the highest molecular mass;
   (b) from 0.5% to 45% by mass, relative to the total mass of the components a), b) and c), of components bearings a single isocyanurate functional group with a molecular mass of not more than three times the average molecular mass of said isocyanate monomers having the highest molecular mass;
   the molar ratio of (a)/(b) being between 0.02 and 2,
   (c) at least 40% by mass, relative to the mass of the components a), b) and c), of a mixture of polyisocyanate compounds having a molecular mass at least equal to three times the average molecular mass of the isocyanate monomers having the smallest molecular mass and bearing at least two isocyanate functional groups, and
   said mixture comprising
   (i) compounds bearing at least two isocyanurate functional groups, excluding those comprising uretidinedione functions,
   (ii) compounds bearing at least two uretidinedione functional groups, excluding those comprising isocyanurate functions and for which the number of monomer units is less than 5,
   (iii) compounds bearing at least two isocyanurate functional group and at least one uretidinedione functional group, having a molecular mass greater than three times the highest molecular mass of the above isocyanate monomer compounds;
   said mixture having a ratio: carbonyl functional groups to a uretidinedione ring/carbonyl functional groups belonging to an isocyanurate ring+carbonyl functional groups belonging to a uretidinedione ring, at least equal to 4%;
   d) from 0 to 25% by mass, relative to the mass of the components a), b), c), d) and e), of compounds bearing at least one isocyanurate functional group that are different than a), b) and c); and
   e) from 0 to 10% by mass, relative to the mass of the components a), b), c), d) and e), of impurities;
   said polyisocyanate composition having a functionally of greater than 4.

30. The polysocyanate composition as claimed in claim 5, wherein the component c) represents at least 50% by mass relative to the total mass of the components a)+b)+c).

31. The polyisocyanate composition as claimed in claim 6, wherein the mass ratio [c)(i)+c)(iii)]/b) is greater than 3.

32. The polyisocyanate composition as claimed in claim 31, wherein the mass ratio [c)(i)+c)(iii)]/b) is greater than 4.

33. The polyisocyanate composition as claimed in claim 7, wherein the amount of compounds c)(ii) is less than 20% by weight relative to the total amount of compounds categorized in c).

34. The polyisocyanate composition as claimed in claim 33, wherein the amount of compounds c)(ii) is less than 15% by weight relative to the total amount of compounds categorized in c).

35. The polyisocyanate composition as claimed in claim 9, wherein the component e) represents from 0.1% to 8% by mass relative to the total mass of the components a)+b)+c)+d)+e).

36. The polyisocyanate composition as claimed in claim 35, wherein the component e) represents not more than 5% by mass relative to the total mass of the components a)+b)+c)+d)+e).

37. The polyisocyanate composition as claimed in claim 12, wherein said isocyanate monomer(s) represent(s) from 0.1% to 10% by mass or the mass of the components a)+b)+c)+d)+e).

38. The polyisocyanate composition as claimed in claim 37, wherein said isocyanate monomer(s) represent(s) not more than 2% by mass at the mass of the components a)+b)+c)+d)+e).

39. The polyisocyanate composition as claimed in claim 38, wherein said isocyanate monomer(s) represent(s) not more than 1% by mass of the mass of the components a)+b)+c)+d)+e).

40. The composition as claimed in claim 13, further comprising an amount of not more than 100% by mass of a)+b)+c)+d)+e), of an organic solvent or mixture of organic solvents as defined in claim 13.

41. The composition as claimed in claim 13, further comprising an amount of not more than 50% of an organic solvent or mixture of organic solvents as defined in claim 13.

42. The composition as claimed in claim 15, comprising from 10% to 100% of the NCO groups present in the composition masked using a masking agent.

43. The process as claimed in claim 19, wherein process step (iii) is carried out until a degree of conversion of isocyanate monomers present in the starting reaction medium of at least 40% is achieved.

44. The process as claimed in claim 20, wherein process step (iii) is carried out until a degree of conversion of isocyanate monomer present in the starting reaction medium of at least 40% is achieved.

* * * * *